US010675065B2

(12) United States Patent
Hopkins et al.

(10) Patent No.: US 10,675,065 B2
(45) Date of Patent: Jun. 9, 2020

(54) BONE SCREW EXTENDER REATTACHMENT SYSTEM AND METHODS

(71) Applicant: Warsaw Orthopedic, Inc., Warsaw, IN (US)

(72) Inventors: Timothy E. Hopkins, San Angelo, TX (US); Larry T. McBride, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1209 days.

(21) Appl. No.: 14/972,963

(22) Filed: Dec. 17, 2015

(65) Prior Publication Data

US 2016/0100866 A1    Apr. 14, 2016

Related U.S. Application Data

(62) Division of application No. 13/280,537, filed on Oct. 25, 2011, now Pat. No. 9,241,743.

(51) Int. Cl.
*A61B 17/70*    (2006.01)

(52) U.S. Cl.
CPC ........ *A61B 17/7086* (2013.01); *A61B 17/708* (2013.01); *A61B 17/7082* (2013.01); *A61B 17/7083* (2013.01)

(58) Field of Classification Search
CPC ............ A61B 17/7086; A61B 17/7074; A61B 17/7083; A61B 17/7088; A61B 17/7082; A61B 17/7076; A61B 17/708
USPC ........... 606/104, 99, 278–279, 246, 264–275
See application file for complete search history.

(56) References Cited

U.S. PATENT DOCUMENTS

| | | | |
|---|---|---|---|
| 6,235,031 B1 | 5/2001 | Hodgeman et al. | 606/64 |
| 7,621,918 B2 | 11/2009 | Jackson | 606/86 A |
| 7,695,475 B2 | 4/2010 | Justis et al. | 606/86 A |
| 7,749,233 B2 | 7/2010 | Farr et al. | 606/104 |
| 7,824,413 B2 | 11/2010 | Varieur et al. | 606/99 |
| 7,862,587 B2 | 1/2011 | Jackson | |
| 7,951,175 B2 * | 5/2011 | Chao | A61B 17/7077 606/279 |
| 8,328,817 B2 | 12/2012 | Strauss | 606/102 |
| 8,394,108 B2 * | 3/2013 | McLean | A61B 17/7082 606/104 |
| 2005/0192589 A1 * | 9/2005 | Raymond | A61B 17/7002 606/99 |
| 2009/0264930 A1 | 10/2009 | McBride | |
| 2010/0036443 A1 | 2/2010 | Hutton et al. | |
| 2010/0114108 A1 | 5/2010 | Strauss | 606/102 |

(Continued)

FOREIGN PATENT DOCUMENTS

EP    2198793 A2    2/2010

*Primary Examiner* — David W Bates
*Assistant Examiner* — Marcela I Shirsat

(57) ABSTRACT

A bone screw extender reattachment system including an elongated reattachment rod having a proximal and a distal end. The distal end of the elongated reattachment rod includes a tip configured to attach to a head of a bone screw. The elongated reattachment rod is configured so that a screw extender assembly having an inner sleeve, an outer housing and an extender head can slide over the reattachment rod. The bone screw extender reattachment system also includes a tension plunger having a plunger-type heed and an elongated shaft configured to slide over the reattachment rod so as to communicate with the screw extender assembly.

20 Claims, 17 Drawing Sheets

(56) References Cited

U.S. PATENT DOCUMENTS

| | | |
|---|---|---|
| 2010/0198268 A1 | 8/2010 | Zhang et al. |
| 2011/0172714 A1 | 7/2011 | Boachie-Adjei et al. |
| 2011/0184475 A1 | 7/2011 | Garcia-Bengochea et al. |

* cited by examiner

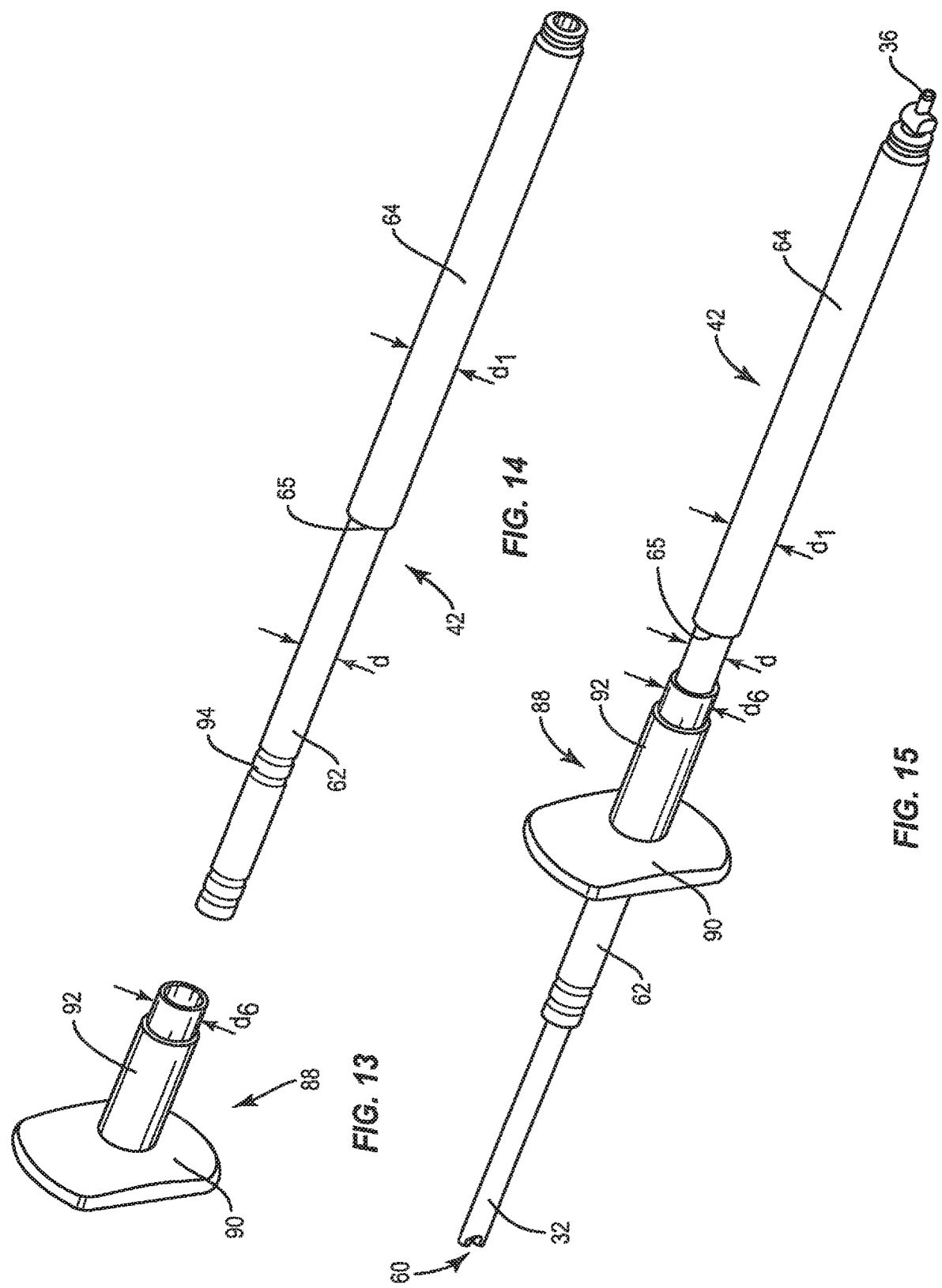

BONE SCREW EXTENDER REATTACHMENT SYSTEM AND METHODS

CROSS-REFERENCE TO RELATED APPLICATIONS

This application is a divisional application of U.S. patent application Ser. No. 13/280,537, filed on Oct. 25, 2011, which is incorporated herein by reference, in its entirety.

TECHNICAL FIELD

The present disclosure generally relates to medical devices for the treatment of musculoskeletal disorders, and more particularly to a bone screw reattachment system, a method for reattaching a screw extender to a screw head in situ, and a method for reattaching a screw extender to a screw heed with a rod already in place.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stress away from a damaged or defective region while healing takes place to restore proper alignment and generally support the vertebral members. During surgical treatment, one or more rods may be attached via one or more bone fasteners to the exterior of one or more vertebral members. This disclosure describes an improvement over these prior art technologies.

SUMMARY OF THE INVENTION

Accordingly, a bone screw extender reattachment system is provided together with methods for reattaching a screw extender to a screw head in situ and reattaching a screw extender to a screw head with a rod already in place. It is contemplated that the extender reattachment system and methods may be employed for scoliosis and kyphosis treatment.

In one particular embodiment in accordance with the principles of the present disclosure, a bone screw extender reattachment system is provided. The bone screw reattachment system includes an elongated reattachment rod having a proximal and a distal end. The distal end of the elongated reattachment rod includes a tip configured to attach to a head of a bone screw. The elongated reattachment rod is configured so that a screw extender assembly having an inner sleeve, an outer housing and an extender head can slide over the reattachment rod. The bone screw extender reattachment system also includes a tension plunger having a plunger-type head and an elongated shaft configured to slide over the reattachment rod so as to communicate with the screw extender assembly.

In one embodiment in accordance with the principles of the present disclosure, a method is provided for reattaching a screw extender to a screw head in situ. The method includes advancing a reattachment rod through the skin of a patient towards the spine to communicate with a head of a screw in the spine. The screw head is then captured by the reattachment rod. A screw extender assembly having an inner sleeve, and outer housing and an extender head and locking tabs is advanced over the reattachment rod until the outer housing engages the screw head. A cannulated tension plunger having a head attached to a cannulated elongated shaft is inserted over the reattachment rod and slid down to contact the inner sleeve and the outer housing. Pressure is applied on the cannulated tension plunger with the locking tabs on the extender head in an open position so that the outer housing is extended distally to engage the screw head. The locking tabs are then manipulated to a locked position so as to lock the screw extender assembly to head of the screw. The plunger and the reattachment rod may then be removed leaving the screw extender assembly attached to the screw head.

In one embodiment in accordance with the principles of the present disclosure, a method is provided for reattaching a screw extender to a screw head with a rod already in place. The method includes advancing a screw extender assembly having an extender and a housing positioned within the extender, wherein the extender comprises an extender head having locking tabs into position with a spine having a screw with a rod positioned therein. A solid tension plunger having a head attached to a solid shaft is inserted into a top portion of the extender head. Pressure is applied on the solid tension plunger so as to apply tension to the housing positioned within the extender so as to manipulate the locking tabs on the extender head to an open or unlocked position to advance the extender distally over the screw head. The locking tabs of the extender are then manipulated into a closed or locked position so as to lock the extender onto the screw head. The solid tension plunger may be removed thereby leaving the extender attached to the screw head.

BRIEF DESCRIPTION OF THE DRAWINGS

The present disclosure will become more readily apparent from the specific description accompanied by the following drawings, in which:

FIG. 13 is a perspective view of a tension plunger in accordance with the principles of the present disclosure;

FIG. 14 is a perspective view of the tension plunger shown in FIG. 13 positioned adjacent the inner sleeve shown in FIG. 7;

FIG. 15 is a perspective view of the tension plunger shown in FIG. 13 and the inner sleeve shown in FIG. 7 inserted over the reattachment rod shown in FIG. 1;

Like reference numerals indicate similar parts throughout the figures.

DETAILED DESCRIPTION OF THE INVENTION

Figure 1:
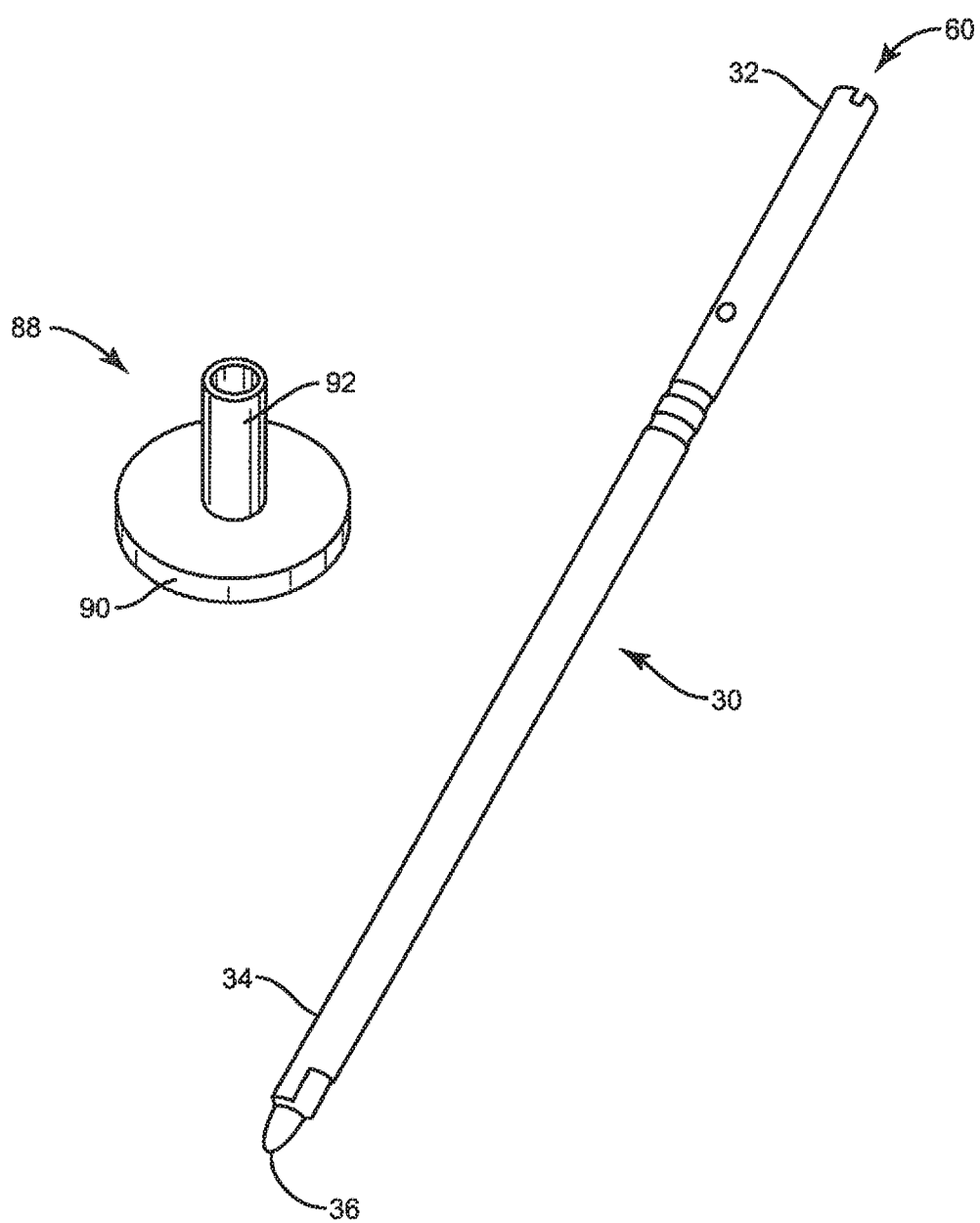
FIG. 1 is a perspective view of one embodiment of a reattachment rod of the bone screw extender reattachment system in accordance with the principles of the present disclosure.
Figure 2:
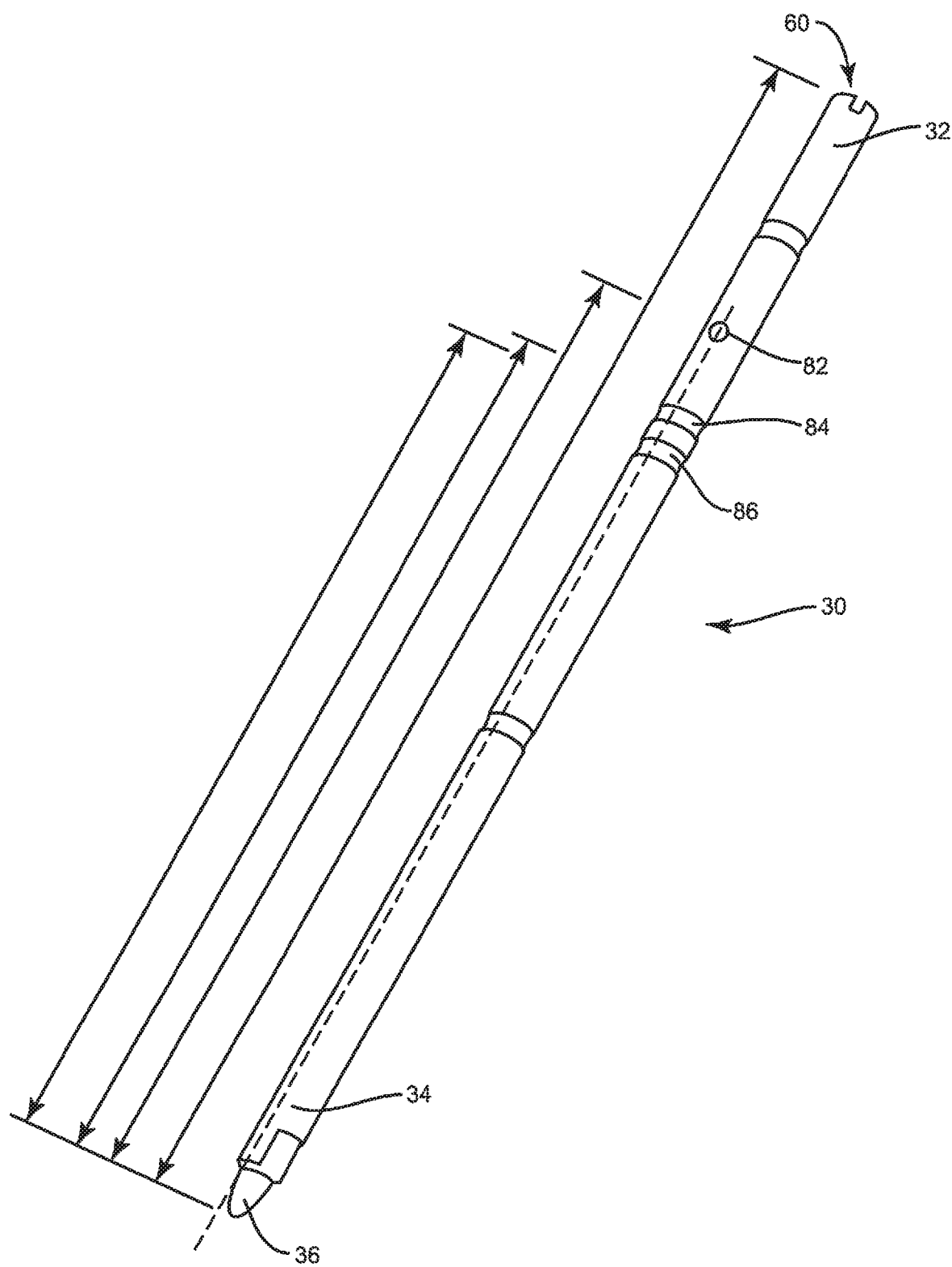
FIG. 2 is a perspective view of the reattachment rod shown in FIG. 1.
Figure 3:
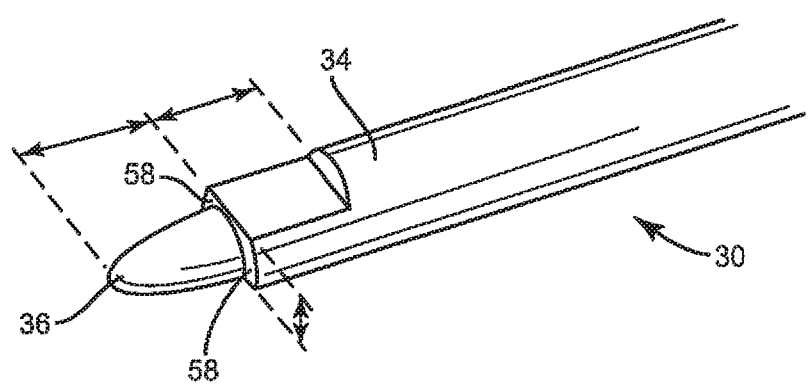
FIG. 3 is a perspective, close up view of a distal end of the reattachment rod shown in FIG. 1.
Figure 4:
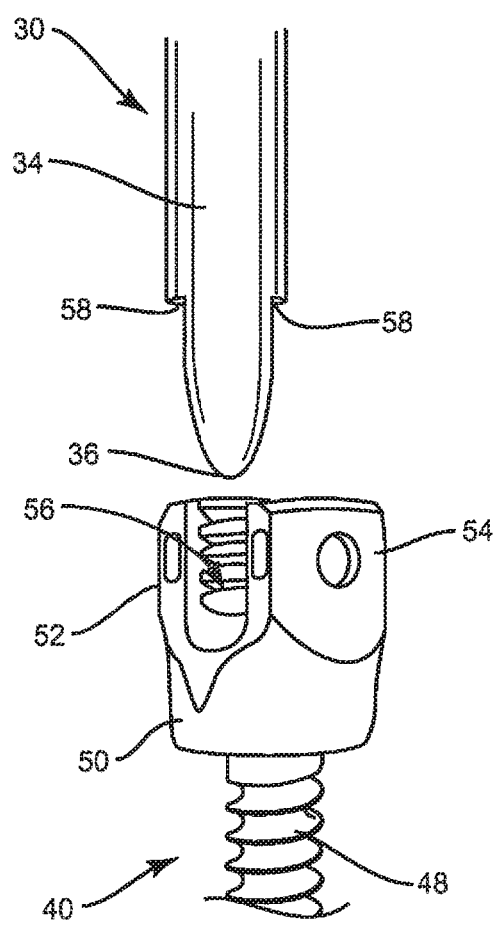
FIG. 4 is a perspective view of the distal end of the reattachment rod shown in FIG. 3 positioned adjacent to a multiaxial bone screw in accordance with the principles of the present disclosure.
Figures 5, 6, 7:
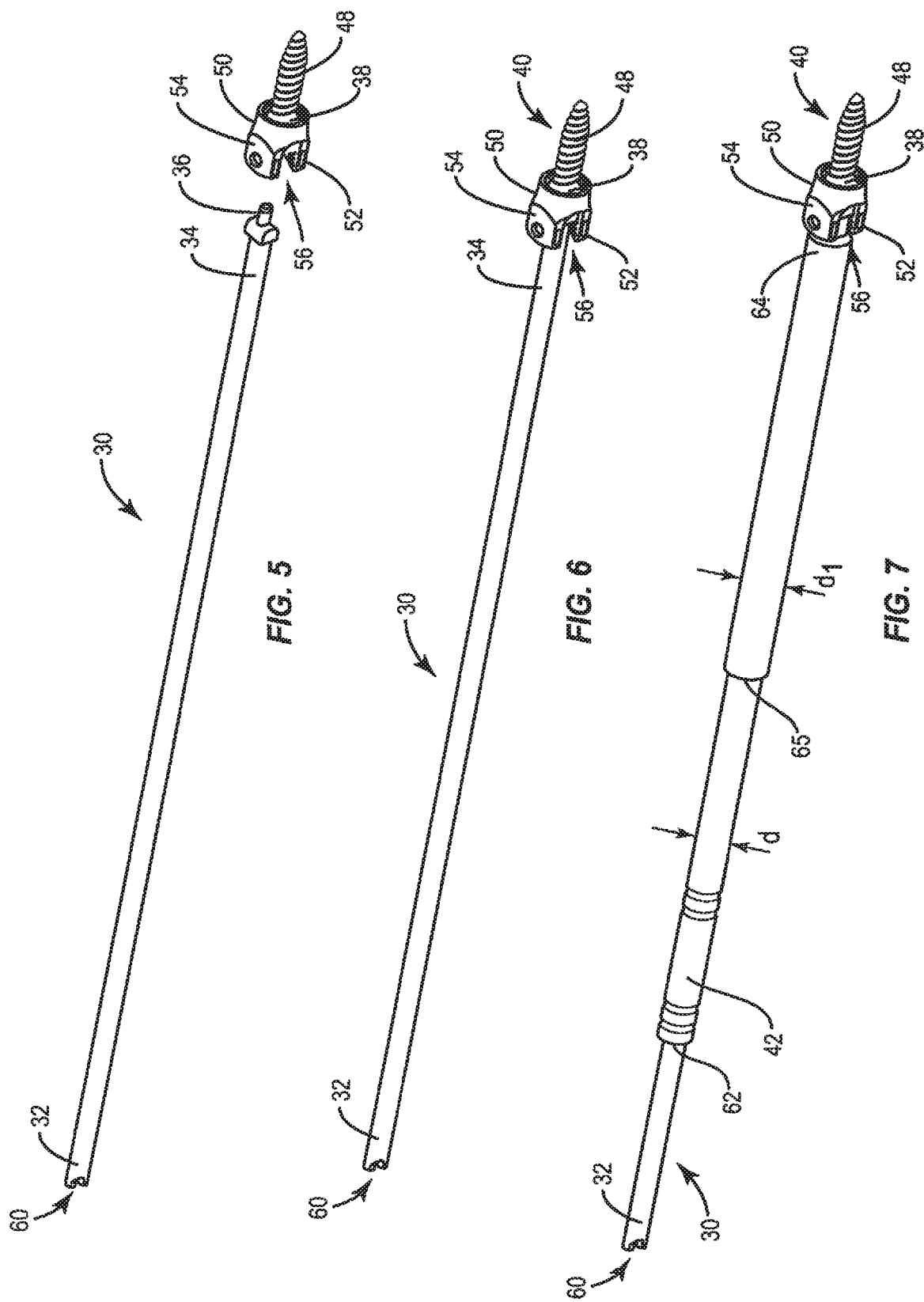
FIG. 5 is a perspective view of the reattachment rod shown in FIG. 1 positioned adjacent to the multiaxial bone screw shown in FIG. 4.
FIG. 6 is a perspective view of the reattachment rod shown in FIG. 1 engaged with the multiaxial bone screw shown in FIG. 4.
FIG. 7 is a perspective view of the reattachment rod shown in FIG. 1 engaged with the multiaxial bone screw shown in FIG. 4 in which the reattachment rod is inserted into an inner sleeve in accordance with the principles of the present disclosure.
Figure 8:
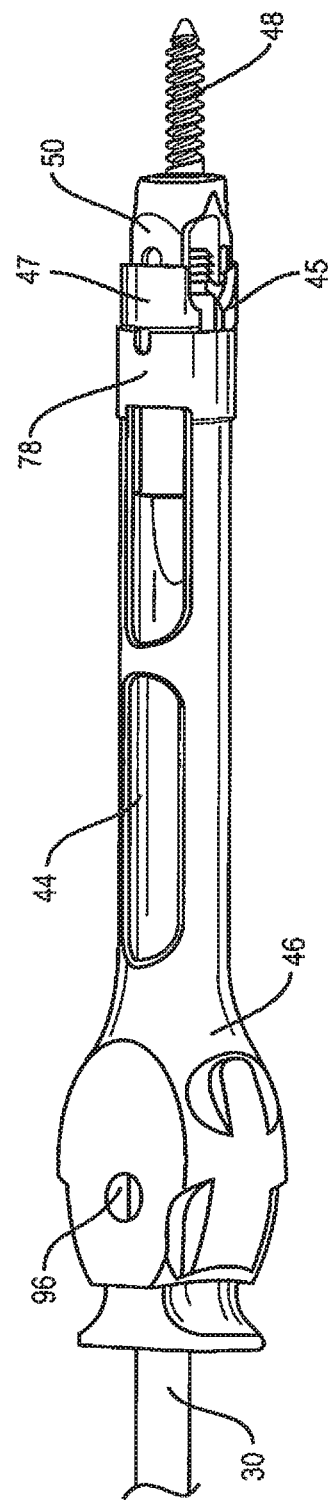
FIG. 8 is a side view of the reattachment rod shown in FIG. 1 engaged with the multiaxial bone screw shown in FIG. 4 in which the reattachment rod is inserted into the inner sleeve shown in FIG. 7 in which the inner sleeve is inserted into an outer housing and an extender head in accordance with the principles of the present disclosure.

The exemplary embodiments of the bone screw extender reattachment system and related methods of use disclosed herein are discussed in terms of medical devices for the treatment of musculoskeletal disorders and more particularly, in terms of a bone screw extender reattachment system and methods for reattaching a screw extender to a screw head in situ and reattaching a screw extender to a screw head with a rod already in place.

It is envisioned that the bone screw extender reattachment system may permit reattachment of an extender to the head of a bone screw in situ without the need to have a release mechanism held in an open position, while maintaining physical line-of-sight view of the bone screw with a speculum or retractor tube. It is further envisioned that the bone screw extender reattachment system may prevent a head of a bone screw from pivoting relative to a shank of the bone screw in a universal, polyaxial fashion, to facilitate alignment and docking of the extender with the bone screw. It is contemplated that the bone screw extender reattachment system may permit visualization of the head of a bone screw through soft, deep, adipose tissue that is difficult to retract.

It is envisioned that the bone screw extender reattachment system may include components that are connected to or attach to one or more extender, such as, for example, a lateral translation handle. It is further envisioned that the extender(s) may have a quick release mechanism to allow one or more extender to detach from a bone screw. It is envisioned that one or all of the components of the bone screw extender reattachment system may be disposable, peel-pack, pre-packed, and sterile devices. One or all of the components of the bone screw extender reattachment system may be reusable. The bone screw extender reattachment system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed bone screw extender reattachment system and methods may be alternatively employed in a surgical treatment with a patient in a prone or supine position, and/or employ various surgical approaches to the spine, including anterior, posterior, posterior mid-line, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," It will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "Inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a bone screw extender reattachment system, a method for reattaching a screw extender to a screw head in situ, and a method for reattaching a screw extender to a screw head with a rod already in place, in accordance with the principles of the present disclosure. Related components and exemplary methods of employing the bone screw reattachment system in accordance with the principles of the present disclosure as well as alternate embodiments are also disclosed. Reference will now be made in detail to the exemplary embodiments of the present disclosure, which are illustrated in the accompanying figures. Turning now to FIGS. 1-6, there is illustrated components of a bone screw reattachment system in accordance with the principles of the present disclosure.

The components of bone screw extender reattachment system can be fabricated from biologically acceptable materials suitable for medical applications, including metals, synthetic polymers, ceramics and bone material and/or their composites, depending on the particular application and/or preference of a medical practitioner. For example, the components of the bone screw extender reattachment system, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the bone screw extender reattachment system may have material composites, including the above materials, to achieve various desired characteristics such as strength, rigidity, elasticity, compliance, biomechanical performance, durability and radiolucency or imaging preference. The components of the bone screw extender reattachment system, individually or collectively, may also be fabricated from a heterogeneous material such as a combination of two or more of the above-described materials. The components of the bone screw extender reattachment system may be monolithically formed, integrally connected or include fastening elements and/or instruments, as described herein.

The bone screw extender reattachment system of the present disclosure includes an elongated reattachment rod 30 extending between a proximal end 32 and a distal end 34, distal end 34 being configured to engage the head of a bone screw. Reattachment rod 30 provides a unique approach to the problem of reattaching a screw extender once a bone screw is fixed to bone in situ. The unique features of the reattachment rod 30 include, for example, constraining a polyaxial or multiaxial bone screw in a known orientation, allowing a screw extender to be inserted over reattachment rod 30 for docking, and placing screw extenders onto a bone screw in a closed position for initial provisional docking, as will be discussed. It is envisioned that reattachment rod 30 may be used with screw extenders containing threaded nut-type locking mechanisms. It is further envisioned that reattachment rod 30 will allow a surgeon to readily detach extenders when there are multiple extenders in use, facilitating placement of adjacent bone screws without the previous extenders interfering. The extenders can then be reattached in a very predictable fashion prior to reducing a vertebral construct, such as a rod, into the head of a bone screw.

In one embodiment, reattachment rod 30 has a cylindrical cross-section. However, it is envisioned that reattachment rod 30 may have various cross-sectional configurations including, for example, round, oval, polygonal, irregular, consistent, variable, uniform, and non-uniform. In one embodiment, reattachment rod 30 has a diameter which is approximately 5/16" and a length that allows proximal end 32 of reattachment rod 30 to be positioned outside a patient's body, while distal end 34 of reattachment rod 30 is engaged with a bone fastener, such as, for example, a bone screw, when the bone fastener is fully implanted in a vertebra. It is contemplated that reattachment rod 30 or portions thereof, can have various dimensions, for example, with regard to length, width, diameter, and thickness.

A bone screw 40 extends between a head 38 and a shank 48. Shank 48 is configured to attach to bone, such as, for example, one or more vertebrae during surgical treatment of a spinal disorder and has a cylindrical configuration. The proximal end of head 38 includes a recess therein configured to receive at least a portion of distal end 34 of reattachment rod 30. The proximal end of head 38 also includes a longitudinal bore 41, best shown in FIG. 9, extending distally through head 38 into shank 48. In one embodiment, bore 41 extends through the proximal and distal ends of bone screw 40 such that bore 41 defines a passageway from the proximal end of bone screw 40 to the distal end thereof. The recess in the proximal end of head 38 is in communication with bore 41.

Figure 9:
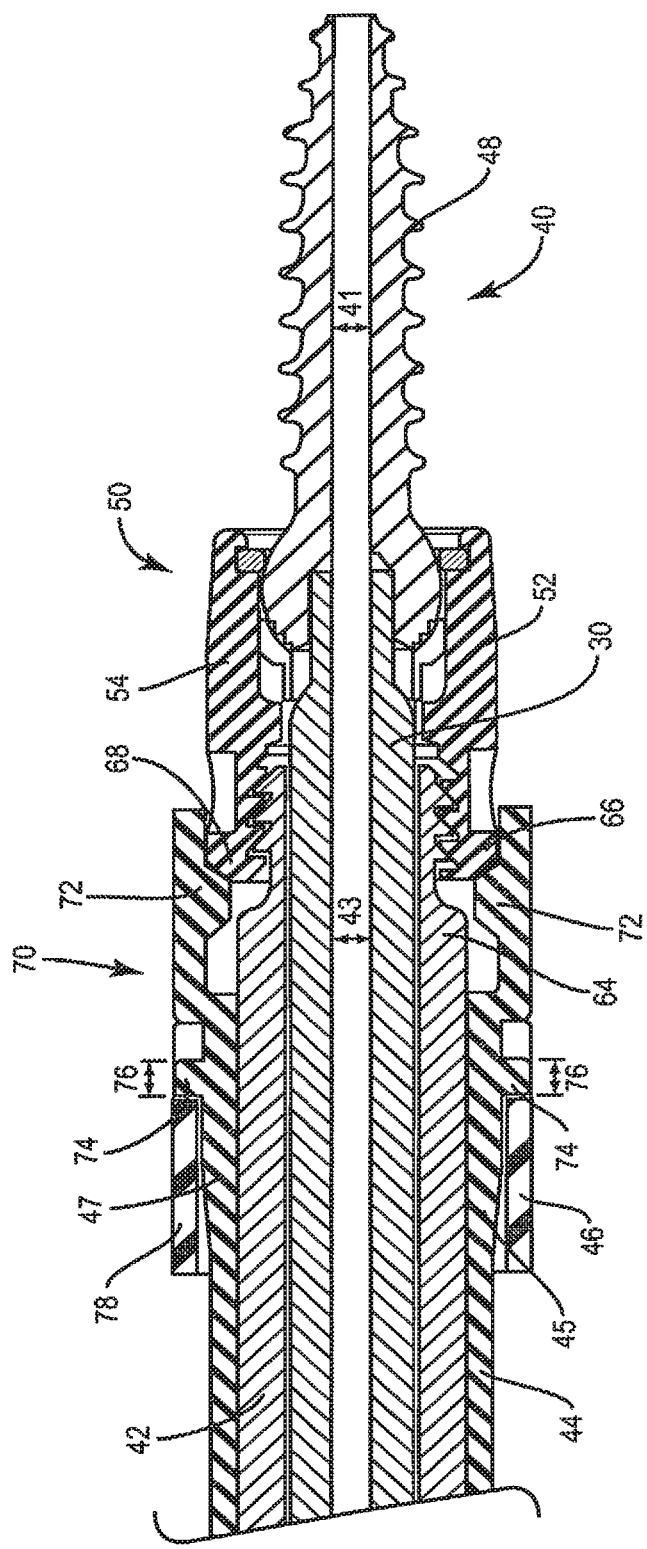
FIG. 9 is side, cross-sectional view of the reattachment rod shown in FIG. 1 engaged with the multiaxial bone screw shown in FIG. 4 in which the reattachment rod is inserted into the inner sleeve shown in FIG. 7 in which the inner sleeve is inserted into the outer housing and the extender head shown in FIG. 9.

In one embodiment, reattachment rod 30 includes a bore 43, best shown in FIG. 9, extending through the length of reattachment rod opening at proximal and distal ends 32, 34 so as to form a passageway from proximal end 32 through the distal end of bone screw 40 when reattachment rod 30 is engaged with bone screw 40. A guidewire may be inserted into bore 43 and/or bore 41 to align reattachment rod 30 with bone screw 40. The proximal end of head 38 further includes a receiver 50 about at least a portion of proximal end of head 38 configured to receive a vertebral construct, such as a vertebral rod. In one embodiment, receiver 50 is defined by an opposing pair of arcuately shaped spaced apart arms 52, 54 defining a U-shaped channel 56 therebetween. U-shaped channel 56 is in communication with the recess in the proximal end of head 38. The interior surfaces of arms 52, 54 include threads configured to mate with the threads of an inner sleeve such that at least a portion of the inner sleeve is engaged with receiver 50, as will be discussed.

Distal end 34 of reattachment rod 30 includes a tip 36 configured to engage head 38 of bone screw 40 such that at least a portion of tip 36 is received or docked within the recess in the proximal end of head 38. In one embodiment, tip 36 has a parabolic shape. It is contemplated that tip 36 can have various dimensions, for example, with regard to length, width, diameter, and thickness. For example, tip 36 may have a configuration which is polygonal, oval, circular, rectangular, square, triangular, parabolic, pointed, and flat, and corresponds to the inside diameter of bone screw 40 such that at least a portion of tip 36 may be received within the recess in the proximal end of head 38. Tip 36 is configured to allow at least some movement between tip 36 and bone screw 40 when tip 36 is received within the recess in the proximal end of head 38. This allows for tactile confirmation of correct docking of tip 36 within the recess in the proximal end of head 38. While at the same time, maintaining the alignment of reattachment rod 30 with bone screw 40. While tip 36 of reattachment rod 30 has a specific configuration, t is the concept of the ability to localize and constrain head 38 with an instrument that would subsequently allow passage of a screw extender over it, onto head 38. Therefore, small modifications in the shape of tip 36, dimensions, or description are contemplated and are within the scope of the present disclosure.

Distal end 34 of reattachment rod 40 includes reliefs 58 extending into the outer surface thereof proximal to tip 36 such that the portion of reattachment rod 40 having reliefs 58 has a thickness which is thinner than the thickness of reattachment rod 40 proximal to reliefs 58. Reliefs 58 define distal faces of reattachment rod 40 configured to engage at least a portion of receiver 50. That is, as tip 36 of reattachment rod 30 is advanced distally through receiver 50 and into the recess in the proximal end of head 38, the distal faces defined by reliefs 58 each engage at least a portion of U-shaped channel 56. In one embodiment, the distal faces defined by reliefs 58 and at least a portion of U-shaped channel 56 form an interface to prevent receiver 50 from pivoting relative to shank 48 of bone screw 40.

Reattachment rod 30 includes a slot 60 extending through proximal end 32. In one embodiment, slot 60 is defined by two opposing spaced apart arms defining a generally U-shaped cavity. Slot 60 is configured to indicate the rotational orientation of bone screw 40. That is, as bone screw 40 is rotated in one direction, slot 60 will be rotated in the same direction. Therefore, slot 60 allows a surgeon to visualize the direction bone screw 40 is rotated as well as the number of rotations.

Referring to FIGS. 7-11, reattachment rod 30 is configured such that a screw extender assembly having an inner sleeve 42, an outer housing 44 and an extender head 46 can slide over reattachment rod 30 when tip 36 of reattachment rod 30 is received within the recess in the proximal end of head 38. Inner sleeve 42 extends between a proximal end 62 and a distal end 64. Inner sleeve 42 has a cylindrical cross-section corresponding to that of reattachment rod 30 and has a diameter which is greater than the diameter of reattachment rod 30 such that inner sleeve 42 can be slid over reattachment rod 30 when tip 36 of reattachment rod is engaged with bone screw 40. That is, reattachment rod 30 and inner sleeve 42 are coaxial. Proximal end 62 has a diameter d and distal end 64 has a diameter $d_1$ which is greater than diameter d. Proximal and distal ends 62, 64 meet to form a ledge 65, best shown in FIG. 7, configured to prevent a plunger from moving distal to ledge 65 along inner sleeve 42, as will be discussed.

Distal end 64 of inner sleeve 42 is configured to be received within receiver 50 and includes threads configured to mate with the threads on the internal surfaces of arms 52, 54 of receiver 50 to engage inner sleeve 42 with receiver 50. That is, after tip 36 of reattachment rod 30 is received within the recess in the proximal end of head 38 to engage reattachment rod 30 with bone screw 40, inner sleeve 42 is inserted over reattachment rod 30 by positioning distal end 64 of inner sleeve 42 over proximal end 32 of reattachment rod 30 and advancing inner sleeve 42 distally until distal end 64 of inner sleeve 42 is received within receiver 50. Inner sleeve 42 may be rotated relative to receiver 50 such that the threads on distal end 64 of inner sleeve 42 mate with the threads on the internal surfaces of arms 52, 54 of receiver 50. Inner sleeve 42 has a length which is less than that of reattachment rod 30 such that when inner sleeve 42 is engaged with receiver 50, at least a portion of reattachment rod 30 is exposed distal to distal end 62 of inner sleeve 42.

Outer housing 44 is defined by arms 45, 47 which converge at a proximal end of outer housing 44 and are spaced apart at a distal end 70 of outer housing 44. Arms 45, 47 are biased such that arms 45, 47 remain spaced apart from one another at distal end 70 of outer housing 44. Outer housing 44 can be slid over inner sleeve 42 when inner sleeve 42 is engaged with receiver 50. Arms 45, 47 are configured to engage receiver 50 such that the inner surfaces of arms 45, 47 mate with the outer surface of receiver 50. In one embodiment, arms 52, 54 of receiver 50 have angled surfaces 66, 68 on the proximal ends thereof configured to engage bosses 72 protruding from the inner surfaces of arms 45, 47 of outer housing 44, best shown in FIG. 9. After inner sleeve 42 is inserted over reattachment rod 30, outer housing 44 may be inserted over inner sleeve 42 by positioning distal end 70 of outer housing 44 over proximal end 32 of reattachment rod 30 and advancing outer housing 44 distally until bosses 72 engage with angled surfaces 66, 68 on receiver 50 to engage outer housing 44 with receiver 50. Outer housing 44 has a length which is less than that of reattachment rod 30 or inner sleeve 42 such that when outer housing 44 is engaged with receiver 50, at least a portion of inner sleeve 42 is exposed distal to distal end 70 of outer housing 44.

Outer housing 44 is configured to accommodate extender head 46 such that extender head 46 can be slid over outer housing 44 and maintained in position relative thereto. In one embodiment, arms 45, 47 of outer housing 44 each include a protrusion 74, best shown in FIG. 9, extending from the outer surfaces of arms 45, 47 configured to be received within a circumferential recess 76 disposed in a distal end 78 of extender head 46. That is, after outer housing 44 is inserted over inner sleeve 42, extender head 46 may be inserted over outer housing 44 by positioning distal end 78 of extender head 46 over proximal end 32 of reattachment rod 30 and advancing extender head 46 distally until at least a portion of protrusions 74 of arms 45, 47 are received within recess 76 of extender head 46 to engage outer housing 44 with extender head 46.

Figure 10:
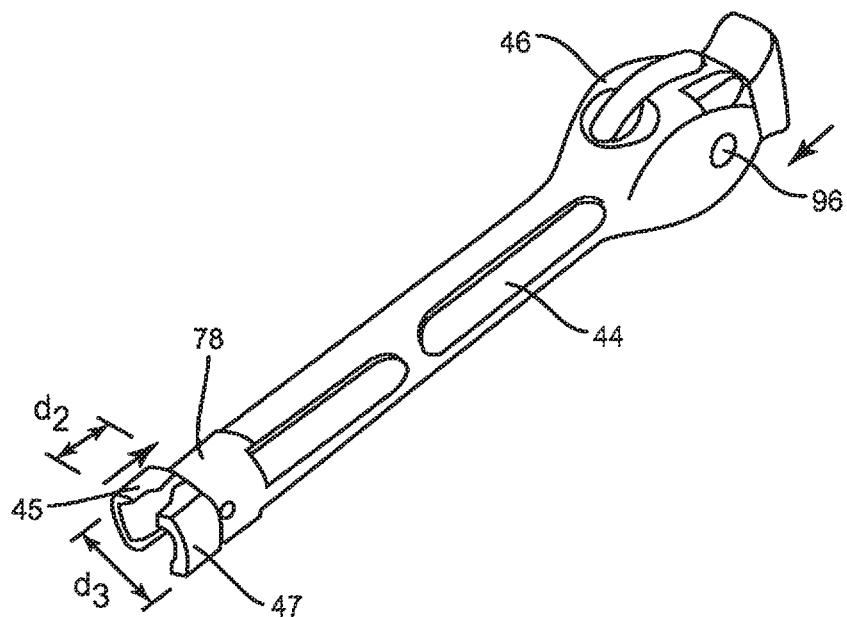
FIG. 10 is a perspective view of a bone screw reattachment system in accordance with the principles of the present disclosure in which the extender head shown in FIG. 8 is in a closed position.
Figure 11:
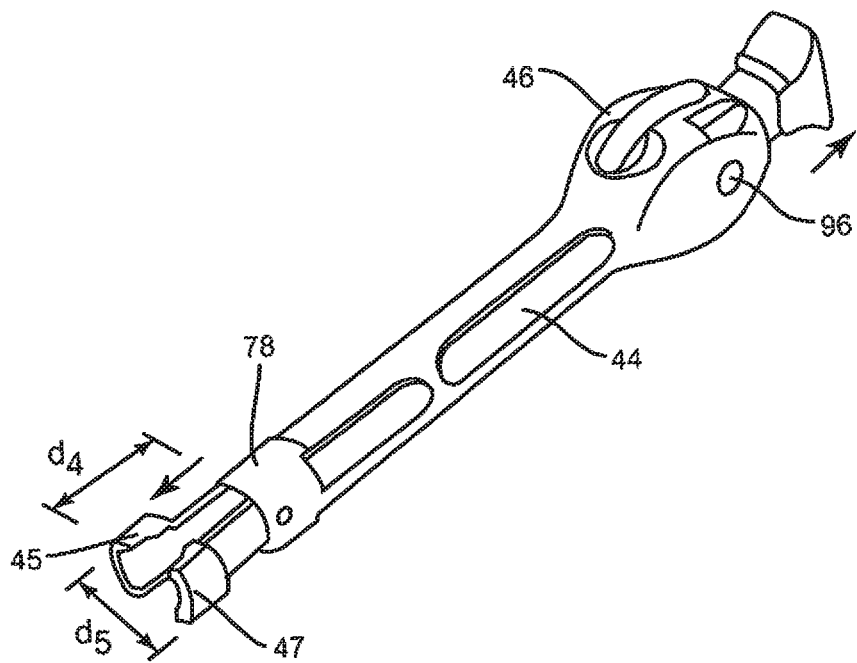
FIG. 11 is a perspective view of the bone screw reattachment system shown in FIG. 10 in which the extender head shown in FIG. 8 is in an open position.

Extender head 46 includes at least one locking tab 96 moveable between a closed or locked position and an open or unlocked position. When locking tab 96 is in the closed position, protrusions 74 are received within recess 76 such that arms 45, 47 extend a distance $d_2$ from distal end 78 of extender head 46 and arms 45, 47 are separated by a distance $d_3$, as shown in FIG. 10. Moving locking tab 96 to the open or unlocked position causes arms 45, 47 to converge at distal end 70 of outer housing 44 such that protrusions 74 are removed from recess 76 allowing outer housing 44 to move distally relative to extender head 46 such that arms 45, 47 extend a distance $d_4$ from distal end 78 of extender head 46, distance $d_4$ being greater than distance $d_2$, and arms 45, 47 are separated by a distance $d_5$, as shown in FIG. 11, distance $d_5$ being greater than distance $d_3$. The screw extender assembly is configured to be positioned adjacent receiver 50 of bone screw 40 when locking tab 96 is in the open or unlocked position and captures receiver 50 when locking tab 96 is moved to the closed or locked position to engage and lock the screw extender assembly with bone screw 40.

Figure 12:
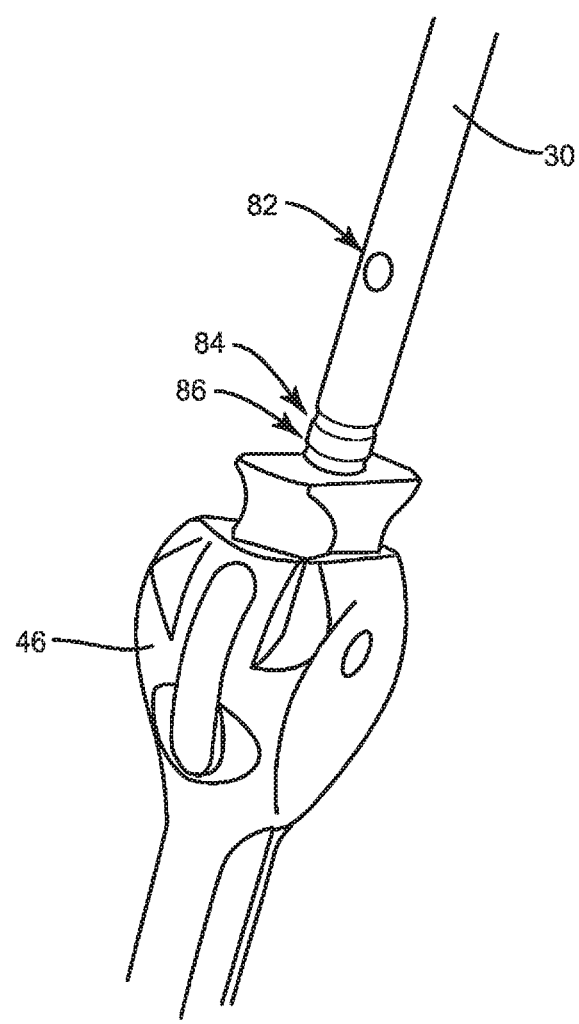
FIG. 12 is a perspective, close up view of a portion of the bone screw reattachment system shown in FIG. 10.
Figure 16:
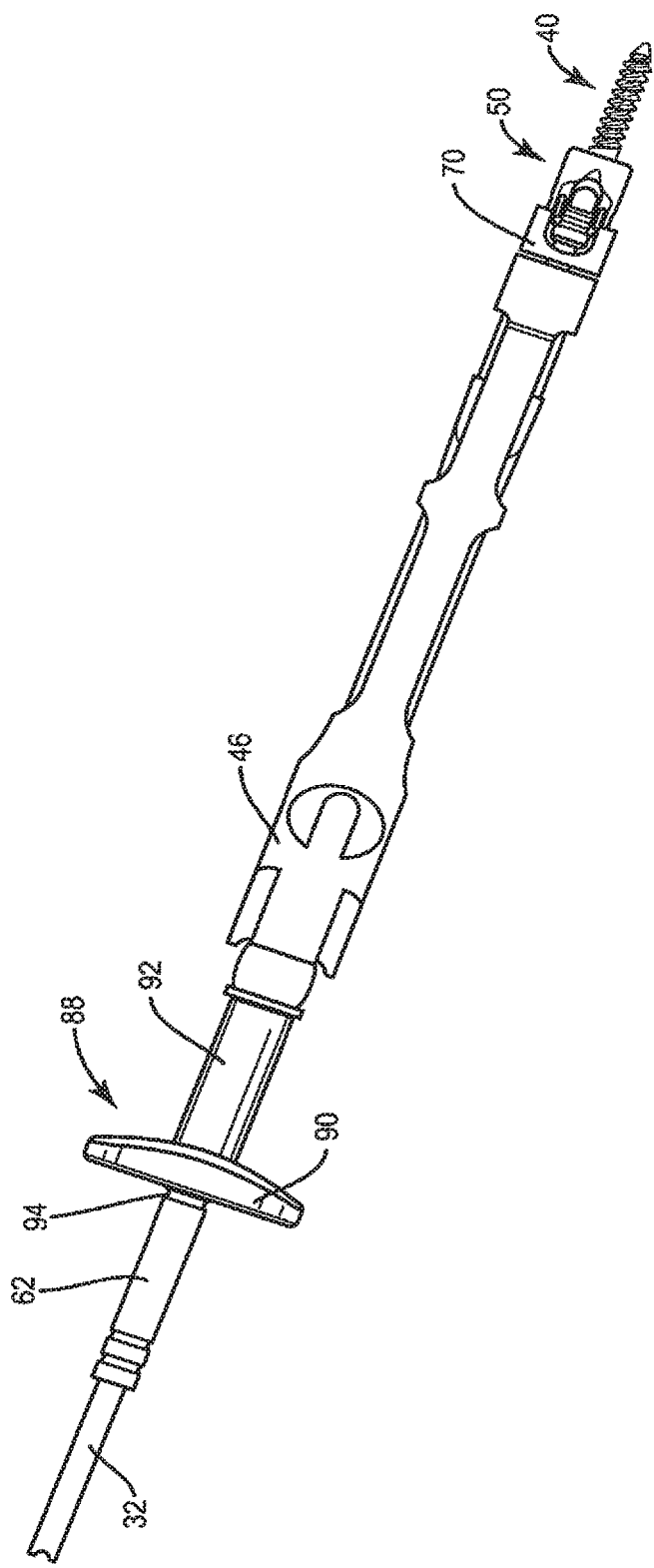
FIG. 16 is a side view of the bone screw reattachment system shown in FIG. 10.

In one embodiment, shown in FIG. 12, reattachment rod 30 includes at least one alignment mark, such as for example, a dot 82 positioned proximal to extender head 46 when at least a portion of protrusion 74 of outer housing 44 is received within recess 76 of extender head 46 to engage outer housing 44 with extender head 46. Dot 82 is configured to correspond to the orientation of extender head 46 so as to ensure correct initial position of extender head 46 relative to reattachment rod 30. That is, dot 82 is set at a defined distance from distal end 34 of reattachment rod 30 so as to indicate alignment of extender head 46 relative to reattachment rod 30. Because slot 60 indicates the orientation of reattachment rod 30 relative to bone screw 40, knowing the orientation of extender head 46 relevant to reattachment rod 30 indicates the orientation of extender head relative to bone screw 40. Reattachment rod 30 may also include first and second circumferential depth marks 84, 86 positioned distal to dot 82, second circumferential depth mark 86 being distal to first circumferential depth mark 84. First and second circumferential depth marks 84, 86 are separated a distance to allow for visual confirmation of appropriate preliminary docking of extender head 46, as well as confirmation of the correct definitive position of the extender head 46 once docked. That is, first and second circumferential depth marks 84, 86 may be used to indicate the amount in which extender head 46 has been extended relative to bone screw 40. Accordingly, the bone screw extender reattachment system may be utilized without line-of-sight or fluoroscopy to locate and/or orient head 38 of bone screw 40.

In one embodiment, inner sleeve 42, outer housing 44 and/or extender head 46 of the screw extender assembly are integral with one another. That is, inner sleeve 42, outer housing 44 and/or extender head 46 may be one single unit. It is envisioned that inner sleeve 42, outer housing 44 and extender head 46 of the screw extender assembly may also be separate components which may be pre-assembled. In one embodiment, the bone screw extender reattachment system may include fastening elements, which may include a locking structure, for assembling, attaching, or connecting inner sleeve 42, outer housing 44 and/or extender head 46. It is envisioned that the locking structure may include fastening elements such as, for example, clips, hooks, adhesives and/or flanges.

As shown in FIGS. 13-19, the bone screw reattachment system includes a tension plunger 88 having a plunger-type head 90 and an elongated shaft 92 configured to communicate with the screw extender assembly. Shaft 92 is hollow and has an opening at a distal end thereof so as to define a cannula. In one embodiment, head 90 has a thickness of approximately 3/16" and shaft 92 has a length of approximately 1 1/8". Shaft 92 has a cylindrical cross-section corresponding to that of inner sleeve 42 and a diameter which is greater than that of inner sleeve 42 such that tension plunger 88 may be inserted over inner sleeve 42. That is, proximal end 62 of inner sleeve 42 is positioned adjacent to shaft 92 of tension plunger 88, or vice versa. Tension plunger 88 is then advanced distally such that proximal end 62 of inner sleeve 42 is received within shaft 92 until proximal end 62 extends through head 90 of tension plunger 88, as shown in FIG. 15. In one embodiment, shaft 92 has a diameter $d_6$ which is greater than diameter d of proximal end 62 of inner sleeve 42 but less than diameter $d_1$ of distal end 64 of inner surface 42 such that tension plunger 88 is prevented from being advanced distal to ledge 65 of inner sleeve 42. In one embodiment, inner sleeve 42 includes a radial groove 94, best shown in FIG. 16, configured to indicate when tension plunger 88 is properly inserted over inner sleeve 42. It is contemplated that tension plunger 88 or portions thereof can have various dimensions, for example, with regard to length, width, diameter, and thickness.

Figure 17:
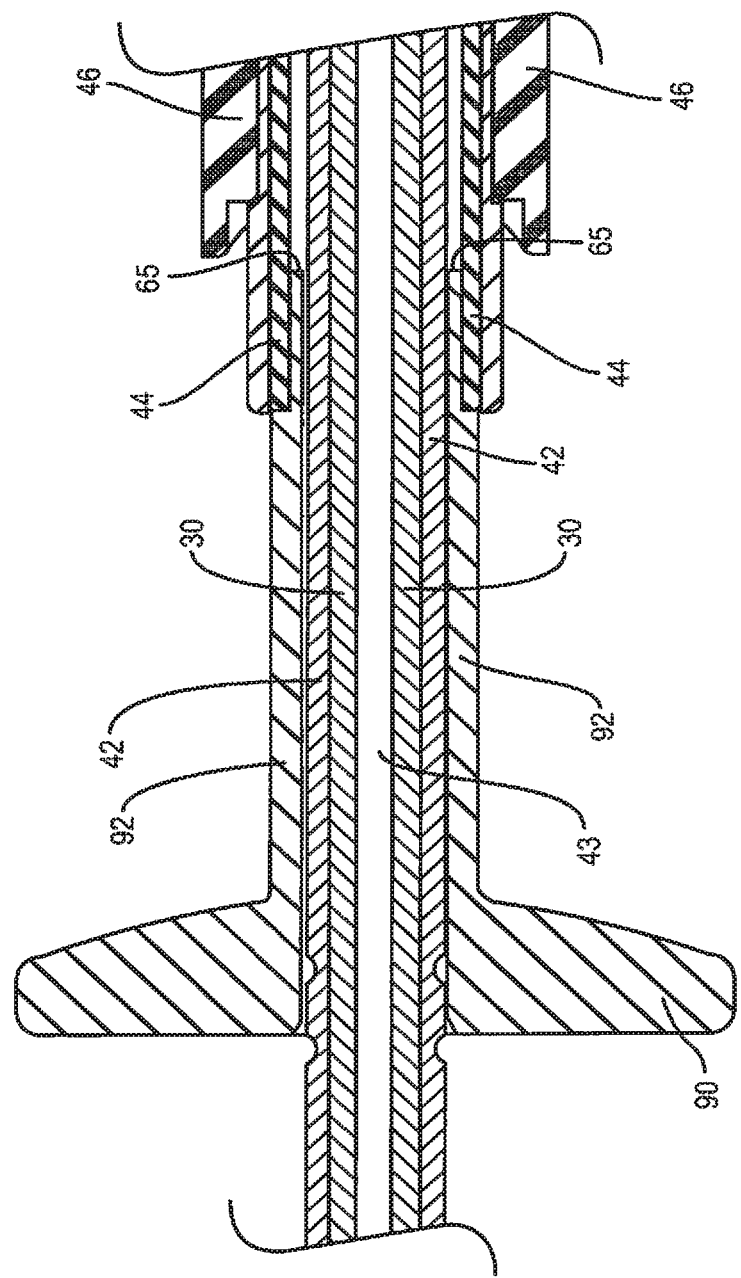
FIG. 17 is a side, cross-sectional view of a distal end of the bone screw reattachment system shown in FIG. 10.
Figure 18:
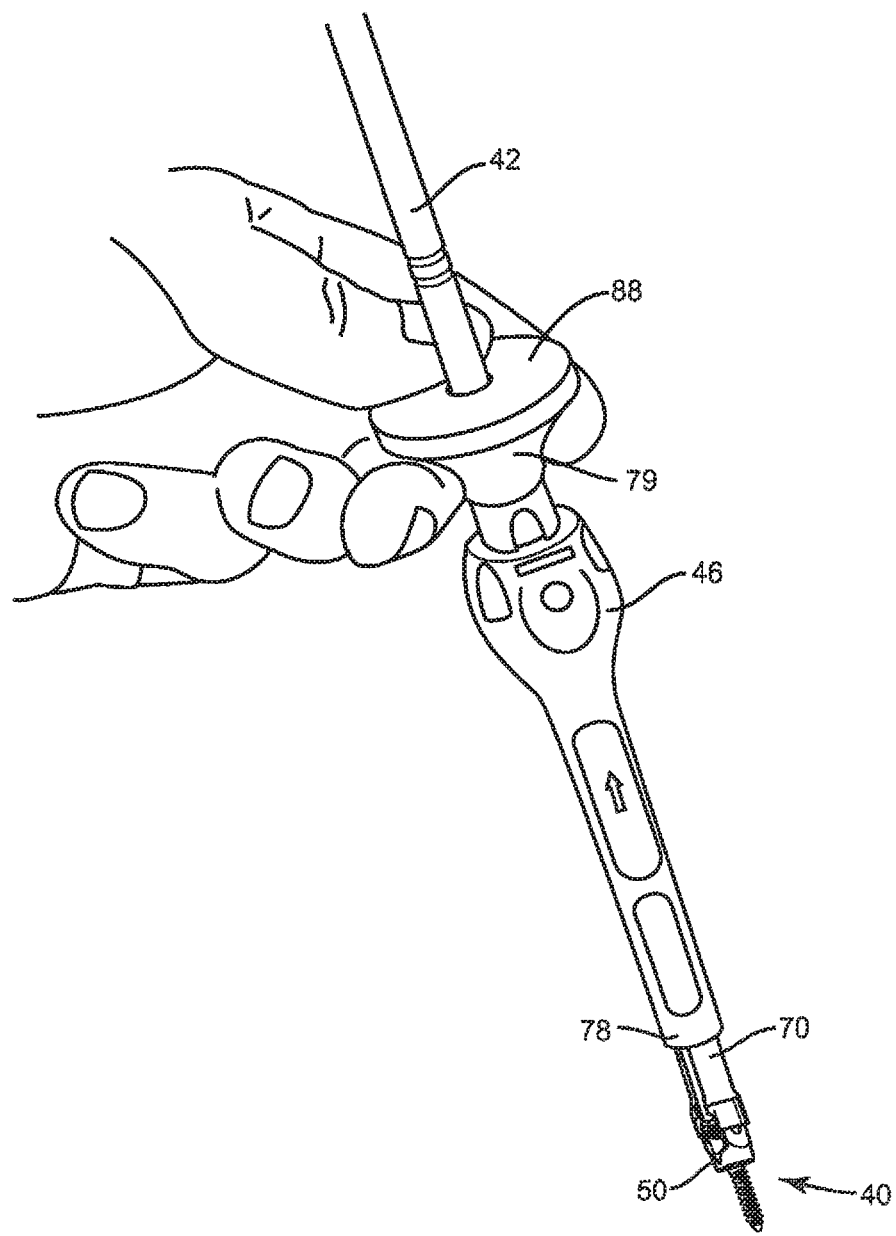
FIG. 18 is a perspective view of the bone screw reattachment system shown in FIG. 10 in use in which the bone screw extender reattachment system is in an open position.
Figure 19:
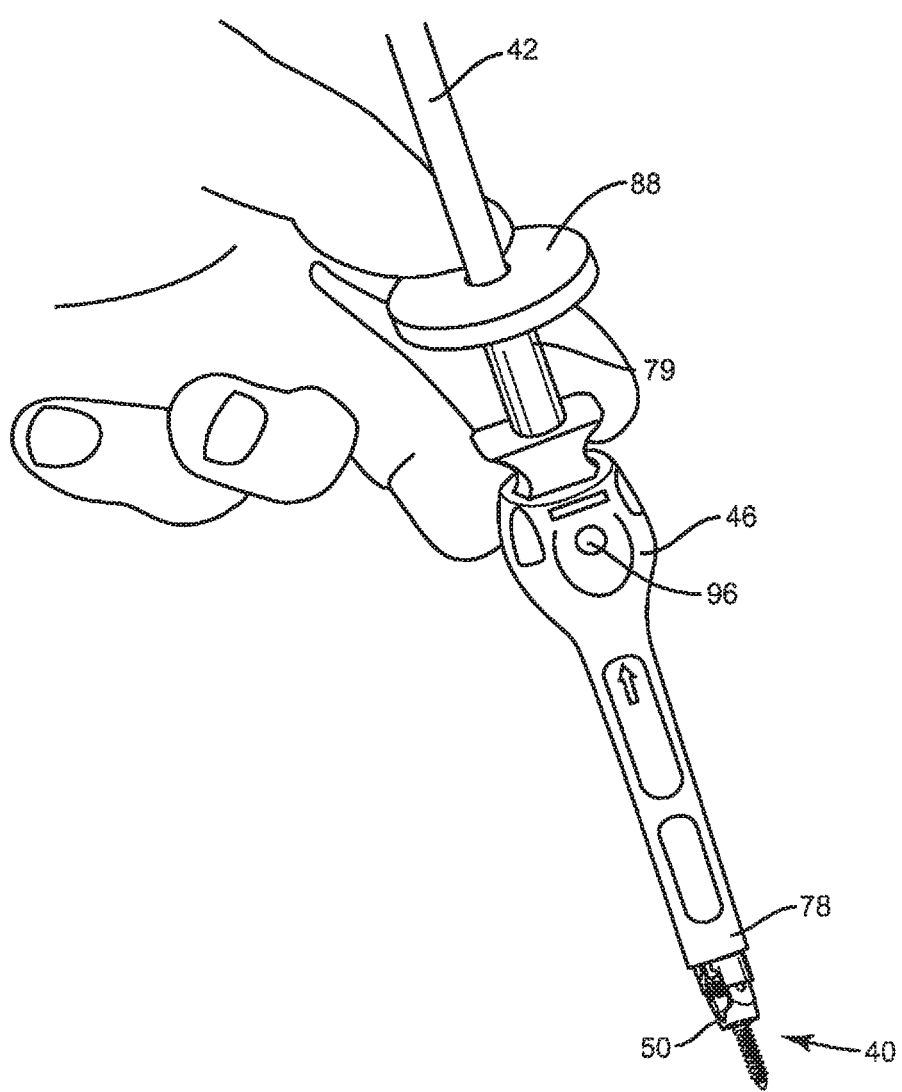
FIG. 19 is a perspective view of the bone screw reattachment system shown in FIG. 10 in use in which the bone screw extender reattachment system is in a closed position.

Tension plunger 88 is configured to slide precisely over reattachment rod 30 and within an interior surface of extender head 46. Tension plunger 88 contacts ledge 65 of inner sleeve 42 and an inner diameter of outer housing 44, as best shown in FIG. 17, to transmit direct tension along outer housing 44 to bone screw 40 when tension plunger 88 is advanced distally. Inner sleeve 42 and reattachment rod 30 may be released from bone screw 40 without disturbing the alignment between outer housing 44 and bone screw 40 and/or extender head 46 and outer housing 44. Thus, applying pressure to tension plunger 88 while pulling up on proximal end 79 of extender head 46 while locking tab 96 is in an open position causes distal end 70 of outer housing 44 to move distally relative to extender head 46 such that distal end 70 of outer housing 44 is distal to distal end 78 of extender head 46. That is, tension plunger 88 is advanced distally which causes outer housing 44 to move distally such that bosses 72 on the inner surfaces of arms 45, 47 of outer housing 44 engage angled surfaces 66, 68 on the proximal ends of arms 52, 54 of receiver 50 to engage outer housing 44 with receiver 50. Once receiver 50 and outer housing 44 are engaged with one another, locking tab 96 may be moved to the locked position to lock the screw extender assembly to receiver 50 such that distal end 78 of extender head 46 engages at least a portion of bone screw 40, as shown in FIG. 19. Tension plunger 88 and reattachment rod 30 may removed, leaving outer housing 44 attached to receiver 50. Accordingly, tension plunger 88 allows tension to be applied along the screw extender assembly to bone screw 40, allowing the screw extender assembly to engage bone screw 40 without losing the stability and orientation of bone screw 40.

The bone screw extender reattachment system of the present disclosure may be used to reattach a screw extender, such as the screw extender assembly discussed hereinabove, to a bone screw, such as bone screw 40 in situ. First, reattachment rod 30 is advanced through the skin of a patient towards the spine to communicate with head 38 of bone screw 40 fixed in the spine. Reattachment rod 30 is then captured by head 38 of bone screw 40 by inserting at least a portion of tip 36 on distal end 34 of reattachment rod 30 into the recess in the proximal end of head 38.

Next, the screw extender assembly including inner sleeve 42, outer housing 44 and extender head 46 are advanced over reattachment rod 30 until arms 45, 47 of outer housing 44 engage receiver 50 of bone screw 40. That is, inner sleeve 42 is engaged with receiver 50 by sliding inner sleeve 42 over reattachment rod 30 and advancing inner sleeve 42 distally. Once distal end 64 of inner sleeve 42 is positioned within receiver 50, inner sleeve 42 may be rotated relative to reattachment rod 30 such that the threads on distal end 64 of inner sleeve 42 mate with the threads on the internal surfaces of arms 52, 54 of receiver 50. As inner sleeve 42 is threaded into receiver 50, outer housing 44 and extender head 46 are advanced until outer housing 44 engages head 38 of bone screw 40. That is, bosses 72 on the inner surfaces of arms 45, 47 of outer housing 44 engage with angled surfaces 66, 68 on receiver 50 to engage outer housing 44 with receiver 50.

Tension plunger 88 is inserted over reattachment rod 30 and is slid distally such that a distal end of shaft 92 contacts ledge 65 of inner sleeve 42 and a proximal end of outer housing 44. Pressure is applied on tension plunger 88 while locking tabs 96 on extender head 46 are in an open position so that extender head 46 is extended distally relative to outer housing 44. Locking tab 96 may be manipulated to a locked position so as to lock the screw extender assembly to the bone screw 40, at which point tension plunger 88 and reattachment rod 30 may be removed, leaving the screw extender assembly attached to head 38 of bone screw 40.

Figure 20:
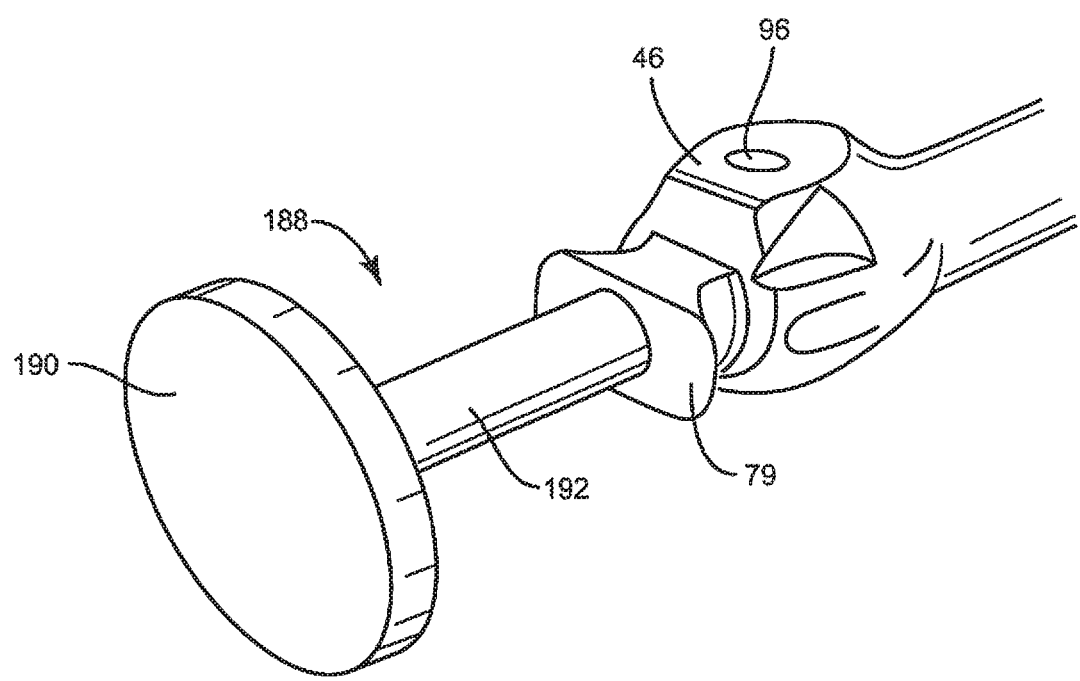
FIG. 20 is a perspective view of one embodiment of the bone screw extender reattachment system in accordance with the principles of the present disclosure.
Figure 21:
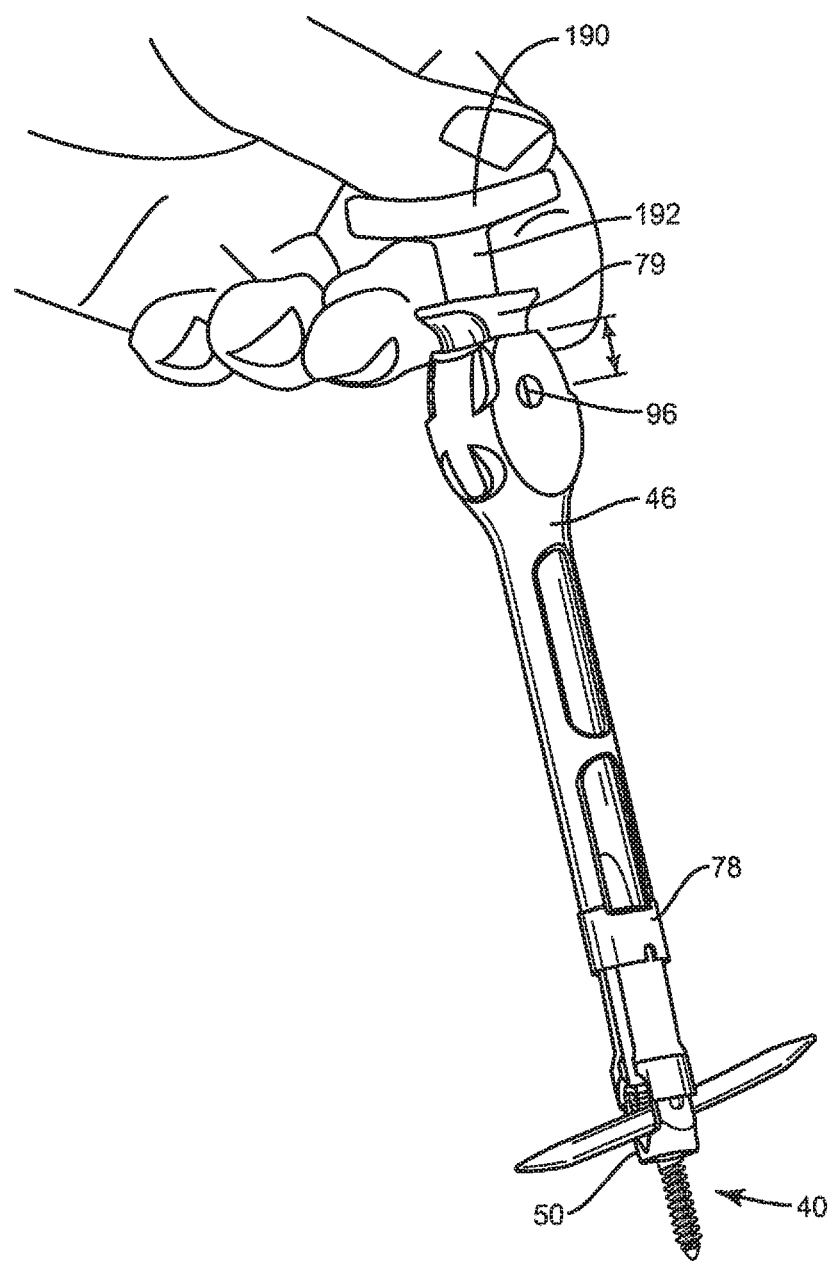
FIG. 21 is a perspective view of the screw extender reattachment system shown in FIG. 20 in an open position.
Figure 22:
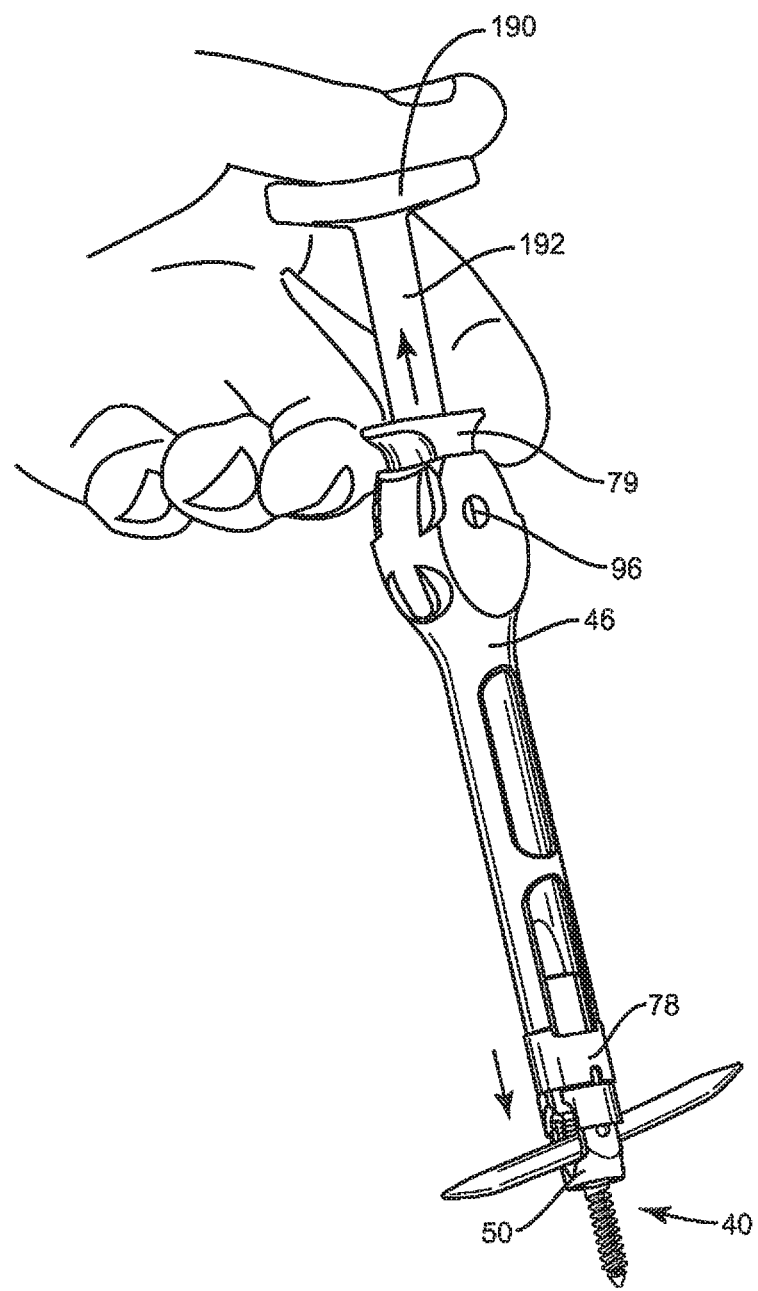
FIG. 22 is a perspective view of the screw extender reattachment system shown in FIG. 20 in a closed position.

In one embodiment, shown in FIGS. 20-22, the screw extender system includes a tension plunger 188 having a configuration similar to that of tension plunger 88 but having a head 190 and a shaft 192 which is solid and configured to be received within an opening extending through a proximal end 79 of extender head 46. That is, shaft 192 of tension plunger 188 has a diameter which is only slightly less than that of an opening in proximal end 79 of extender head 46 (not shown) such that shaft 192 fits closely within the opening. In one embodiment, the diameter of shaft 192 is approximately ⁵⁄₁₆".

Tension plunger 188 having shaft 192 which is solid will allow the bone screw extender reattachment system to reattach an extender to a bone screw where the bone screw already has a vertebral construct, such as a vertebral rod, for example, inserted into a receiver of the bone screw. In particular, the screw extender reattachment system includes a screw extender assembly having an extender, such as, for example, extender head 46 and a housing, such as, for example, outer housing 44, positioned within the extender.

The extender includes at least one locking tab, such as, for example, locking tab 96. Tension plunger 188 is inserted into an opening in a top portion of the extender head, such as an opening in proximal end 79 of extender head 46. The housing is advanced distally such that the housing is positioned adjacent to the bone screw. Pressure is applied on tension plunger 188 so as to apply tension to the housing positioned within the extender while the locking tab on the extender head is in an open position to engage the housing with the screw head, as shown in FIG. 21. The locking tab of the extender is then manipulated into a locked position so as to lock the extender onto the screw head, as shown in FIG. 22. Tension plunger 188 may be removed thereby leaving the extender attached to the screw head.

The bone screw extender reattachment system of the present disclosure may be utilized to reattach extenders to bone screws. It is envisioned that the bone screw extender reattachment system may be utilized in a spinal instrumentation system that allows for image-guided, minimal-access spinal surgery; allowing for percutaneous placement of pedicle screws and connecting rods, as well as their manipulation.

It is envisioned that components of the bone screw extender reattachment system may be coated with biocompatible materials such as an osteoconductive material such as (HA)-TCP and/or osteoinductive agent such as a bone morphogenic protein (BMP) for enhanced bony fixation. It is envisioned that the biocompatible material and/or an agent may include one or more therapeutic agent(s) disposed in one or more layers or homogenously. For example, a component of the bone screw extender reattachment system may include at least one agent including biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as (HA)-TCP, calcium phosphate and calcium sulfite. It is further envisioned that such agents may include, for example, biologically active agents coated onto the exterior of the components of the bone screw extender reattachment system and/or applied thereto for gradual release such as by blending in a bioresorbable polymer that releases the biologically active agent or agents in an appropriate time dependent fashion as the polymer degrades within the patient.

It will be understood that various modifications may be made to the embodiments disclosed herein. Therefore, the above description should not be construed as limiting, but merely as exemplification of the various embodiments. Those sidled in the art will envision other modifications within the scope and spirit of the claims appended hereto.

What is claimed is:

1. A method comprising:
    advancing a rod through skin of a patient and towards a spine of the patient such that a tip of the rod is received within a recess of a screw;
    providing a screw extender assembly comprising an inner sleeve, an outer housing and an extender head, the extender head including locking tabs;
    advancing the screw extender assembly over the rod until the outer housing is adjacent to the screw;
    positioning a shaft of a plunger over the inner sleeve such that the shaft contacts an inner diameter of the outer housing;

translating the plunger relative to the rod such that the plunger contacts a ledge of the inner sleeve and the outer housing translates relative to the screw to engage the screw;

moving the locking tabs from an unlocked position to a locked position so as to lock the screw extender assembly to the screw; and removing the plunger and the rod and leaving the screw extender assembly attached to the screw.

2. The method of claim 1, further comprising aligning a proximal end of the extender head with a mark on the rod so as to provide visual confirmation that the screw extender assembly has engaged the screw without line-of-sight view of the head.

3. The method of claim 1, wherein the locking tabs of the extender head are in the locked position when the screw extender assembly is positioned over the rod.

4. The method of claim 1, wherein force applied on the plunger is transmitted to the inner sleeve when the plunger engages the ledge and translates relative to the rod.

5. The method of claim 1, wherein the rod is manipulated through the skin and towards the spine so as to tactilely feel for when the tip is seated within the recess.

6. The method of claim 1, further comprising moving the locking tabs from the locked position to the unlocked position and disengaging the screw extender assembly from the screw.

7. The method of claim 6, wherein the locking tabs of the extender head are manipulated to a locked position thereby locking the screw extender assembly to the screw and leaving the screw extender assembly attached to the head of the screw.

8. The method of claim 1, wherein the screw is implanted in the spine.

9. The method of claim 1, wherein the shaft of the plunger is cannulated.

10. The method of claim 1, wherein the shaft of the plunger is non-cannulated.

11. The method of claim 1, wherein the outer housing includes a pair of protrusions, the protrusions being received within cavities of the screw when the locking tabs are in the locked position, the protrusions being spaced apart from the cavities when the locking tabs are in the unlocked position.

12. The method of claim 1, wherein the extender head is positioned over the outer housing.

13. A method comprising:

inserting a tip of a rod into a recess of a screw;

providing a screw extender assembly comprising an inner sleeve and an outer housing;

positioning the screw extender assembly over the rod;

positioning a shaft of a plunger over the inner sleeve;

translating the plunger relative to the rod such that the plunger contacts a ledge of the inner sleeve and the outer housing translates relative to the screw to engage the screw and attach the screw extender assembly to the screw; and removing the plunger and the rod and leaving the screw extender assembly attached to the screw.

14. The method of claim 13, wherein positioning the shaft over the inner sleeve positions the shaft between an outer diameter of the inner sleeve and an inner diameter of the outer housing.

15. The method of claim 13, wherein the screw extender assembly comprises an extender head, the extender head including locking tabs, the locking tabs being moved from an unlocked position to a locked position with the screw extender assembly attached to the screw so as to lock the screw extender assembly to the screw.

16. The method of claim 15, wherein the extender head is positioned over the outer housing.

17. The method of claim 15, further comprising:

moving the locking tabs from the locked position to the unlocked position to unlock the screw extender assembly;

disengaging the screw extender assembly from the screw.

18. A method comprising:

inserting a tip of a rod into a recess of a screw;

providing a screw extender assembly comprising an inner sleeve, an outer housing and an extender head positioned over the outer housing, the outer housing including spaced apart arms, the arms each including a projection, the extender head including locking tabs;

positioning the screw extender assembly over the rod;

positioning a shaft of a plunger over the inner sleeve such that the shaft is positioned between an outer diameter of the inner sleeve and an inner diameter of the outer housing;

translating the plunger relative to the rod such that the plunger contacts a ledge of the inner sleeve and the outer housing translates relative to the screw to engage the screw and attach the screw extender assembly to the screw;

moving the locking tabs from an unlocked position in which the projections are spaced apart from cavities of the screw to a locked position in which the projections are disposed in the cavities; and removing the plunger and the rod and leaving the screw extender assembly attached to the screw.

19. The method of claim 18, further comprising:

moving the locking tabs from the locked position to the unlocked position to unlock the screw extender assembly;

disengaging the screw extender assembly from the screw.

20. The method of claim 18, wherein the screw is implanted in a patient.

* * * * *